United States Patent [19]
Sussman et al.

[11] Patent Number: 6,004,284
[45] Date of Patent: Dec. 21, 1999

[54] SURGICAL HANDPIECE

[75] Inventors: Glenn Sussman, Lake Forest, Calif.; Thomas G. Capetan, Fort Worth, Tex.

[73] Assignee: Alcon Laboratories, Inc.

[21] Appl. No.: 09/266,501

[22] Filed: Mar. 11, 1999

Related U.S. Application Data

[63] Continuation-in-part of application No. 09/090,433, Jun. 4, 1998.

[51] Int. Cl.⁶ .................................................. A61M 1/00
[52] U.S. Cl. ........................................ 604/27; 604/152
[58] Field of Search ............................ 604/27, 113–114, 604/131, 140, 141, 143, 151–152; 607/96, 98–99, 113–114

[56]    References Cited

U.S. PATENT DOCUMENTS

| | | |
|---|---|---|
| 3,818,913 | 6/1974 | Wallach . |
| 3,930,505 | 1/1976 | Wallach . |
| 4,024,866 | 5/1977 | Wallach . |
| 4,246,902 | 1/1981 | Martinez . |
| 4,402,817 | 9/1983 | Maget ...................................... 204/301 |
| 4,471,256 | 9/1984 | Igashira et al. ......................... 310/328 |
| 4,570,632 | 2/1986 | Woods . |
| 4,577,629 | 3/1986 | Martinez . |
| 4,597,388 | 7/1986 | Koziol et al. ......................... 128/303.1 |
| 4,857,054 | 8/1989 | Helfer ..................................... 604/102 |
| 4,909,249 | 3/1990 | Akkas et al. . |
| 4,911,161 | 3/1990 | Schechter . |
| 4,915,094 | 4/1990 | Laruche et al. ........................... 128/24 |
| 4,986,827 | 1/1991 | Akkas et al. . |
| 5,019,035 | 5/1991 | Missirlian et al. . |
| 5,106,364 | 4/1992 | Hayafuji et al. . |
| 5,176,628 | 1/1993 | Charles et al. . |
| 5,226,910 | 7/1993 | Kajiyama et al. . |
| 5,257,977 | 11/1993 | Eschel ...................................... 604/113 |
| 5,261,883 | 11/1993 | Hood et al. ............................. 604/153 |
| 5,275,607 | 1/1994 | Lo et al. . |
| 5,284,472 | 2/1994 | Sussman et al. . |
| 5,285,795 | 2/1994 | Ryan et al. . |
| 5,322,504 | 6/1994 | Doherty et al. . |
| 5,549,559 | 8/1996 | Eshel ....................................... 604/113 |
| 5,562,692 | 10/1996 | Bair ......................................... 606/167 |
| 5,591,184 | 1/1997 | McDonnell et al. ..................... 606/167 |
| 5,624,392 | 4/1997 | Saab .......................................... 604/43 |
| 5,653,692 | 8/1997 | Masterson et al. ..................... 604/113 |
| 5,669,923 | 9/1997 | Gordon . |
| 5,674,226 | 10/1997 | Doherty et al. . |
| 5,713,864 | 2/1998 | Verkaart ................................. 604/113 |
| 5,865,790 | 2/1999 | Blair . |
| 5,879,347 | 3/1999 | Saadat ...................................... 606/28 |
| 5,885,243 | 3/1999 | Capetan et al. ........................... 604/27 |
| 5,891,094 | 4/1999 | Masterson et al. ..................... 604/113 |

*Primary Examiner*—Wynn Wood Coggins
*Assistant Examiner*—LoAn H. Thanh
*Attorney, Agent, or Firm*—Jeffrey S. Schira

[57]    ABSTRACT

A surgical handpiece driver having a pumping chamber. The pumping chamber works by boiling a small volume of a fluid. As the fluid boils, it expands rapidly, thereby propelling a piston down the length of the pumping chamber. The piston may be attached to the operative shaft or rod of a surgical probe and produce reciprocal motion. Alternatively, the piston may be attached to a cam or gear to product rotary motion.

6 Claims, 5 Drawing Sheets

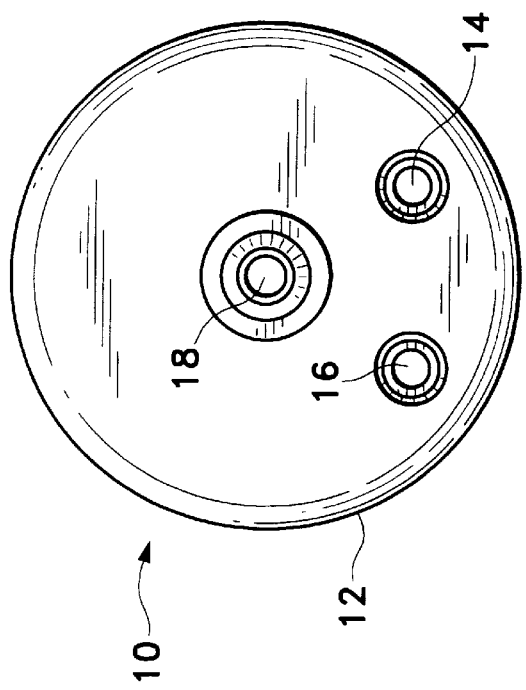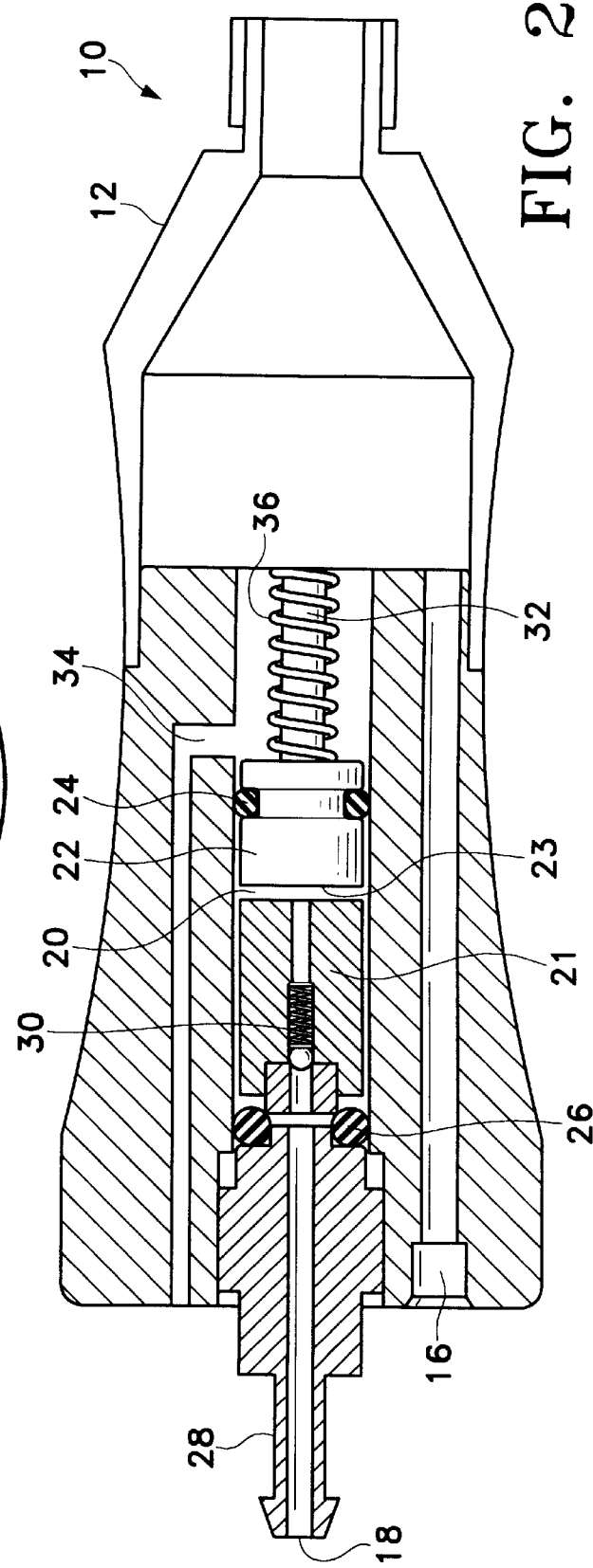

SURGICAL HANDPIECE

This application is a continuation-in-part application of U.S. patent application Ser. No. 09/090,433, filed Jun. 4, 1998.

BACKGROUND OF THE INVENTION

This invention relates generally to the field of ophthalmic surgery and more particularly to a pumping chamber for use with a surgical handpiece.

During many surgical procedures, particularly microsurgical procedures such as ophthalmic surgery, small mechanical devices or probes are inserted into the surgical field. These different probes have a variety of functions. For example, small scissors are often to used to cut fibrous tissue. Guillotine-type or rotary cutters are used to remove the vitreous from the posterior chamber of an eye or for opening the anterior capsule for cataract surgery. Prior to the present invention, these devices have all used pneumatic or electric drivers. Pneumatic drivers use air pressure pulses to force a plunger against a spring. When the pressure pulse decays, the spring forces the plunger back to its original starting point, thereby imparting reciprocal motion to the plunger. With these types of surgical systems, the pressure pulse is generated in the control console and can travel as far as two meters down the connecting pneumatic tubing before entering the probe. Compliance in the tubing causes degradation of the pressure pulse. Electrical drivers contain miniature electrical motors that can be heavy and relatively expensive, making them less desirable for disposable probes.

Therefore, a need continues to exist for a handpiece driver that is lighter, less expensive than the prior art drivers and that delivers sharp, consistent drive pulses, with faster cut rates and/or rise time.

BRIEF SUMMARY OF THE INVENTION

The present invention improves upon the prior art by providing a surgical handpiece driver having a pumping chamber. The pumping chamber works by boiling a small volume of a fluid. As the fluid boils, it expands rapidly, thereby propelling a piston down the length of the pumping chamber. The piston may be attached to the shaft or rod of a surgical probe and produce reciprocal motion. Alternatively, the piston may be attached to a cam or gear to produce rotary motion.

Accordingly, one objective of the present invention is to provide a surgical handpiece having a pumping chamber.

Another objective of the present invention is to provide a surgical handpiece that is lighter than the prior art handpieces.

Another objective of the present invention is to provide a surgical handpiece that is less expensive.

Another objective of the present invention is to provide a surgical handpiece that delivers sharp, consistent drive pulses, with high speed and/or rise time.

Another objective of the present invention is to provide a surgical handpiece having fast cut rates.

Another objective of the present invention is to provide a surgical handpiece having a wide range of cut rates.

These and other advantages and objectives of the present invention will become apparent from the detailed description and claims that follow.

BRIEF DESCRIPTION OF THE DRAWINGS

FIG. 1 is an elevational view of the proximal end of the handpiece of the present invention.

FIG. 2 is a schematic, cross-sectional view of a first embodiment of the handpiece of the present invention.

DETAILED DESCRIPTION OF THE INVENTION

Figure 3:
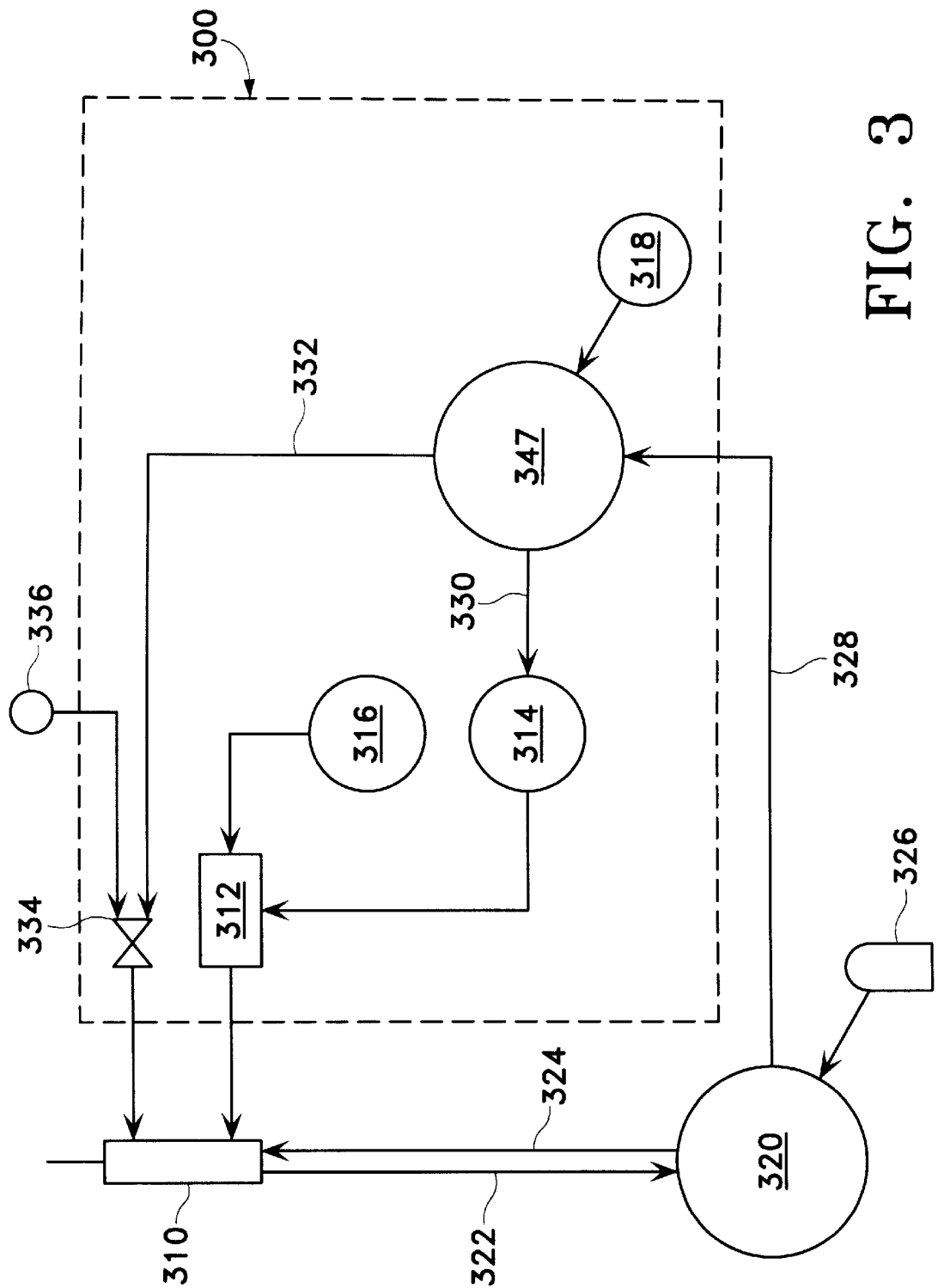
FIG. 3 is a block diagram of a control system that can be used with the surgical handpiece of the present invention.

Handpiece 10 of the present invention generally includes handpiece body 12 having internal irrigation lumen 14, internal aspiration lumen 16 and boiling chamber fluid supply lumen 18. Body 12 may be made from plastic, metal or ceramic.

As best seen in FIG. 2, a first embodiment of handpiece 10 contains pumping chamber 20 formed between electrode 21 and piston 22. A second electrode 23, is formed on the proximal face of piston 22. Piston 22 is sealed within chamber 20 by seal 24 and electrode 21 is sealed within chamber 20 by seal 26 and fluid supply fitting 28.

In operation, pumping chamber 20 is supplied with a conductive fluid (e.g. saline solution) through lumen 18. Electrical current (preferably RFAC) is delivered to and across electrodes 21 and 23 because of the conductive nature of the fluid. As the current flows through the fluid, the fluid boils. As the fluid boils, it expands rapidly and forces piston 22 distally. Check valve 30 prevents the expanding fluid from entering lumen 18. Rod 32, which is connected to piston 22, is forced distally along with piston 22. Piston 22 travels distally until it passes vent port 34, thereby venting the excess pressure from chamber 20, and allowing return spring 36 to force piston 22 back toward electrode 21. Subsequent pulses of electrical current form sequential gas bubbles that impart a reciprocal motion to piston 22 and rod 32. The size and pressure of the fluid pulse obtained by pumping chamber 20 can be varied by varying the length, timing and/or power of the electrical pulse sent to electrodes 21 and 23 and by varying the dimensions of chamber 20. In addition, the fluid may be preheated prior to entering pumping chamber 20. Preheating the fluid will decrease the power required by pumping chamber 20 and/or increase the speed at which pressure pulses can be generated.

Alternatively, pumping chamber 20 and vent port 34 may be interconnected in a sealed system, so that no fluid needs to be added to chamber 20 through lumen 18.

Figure 4A:
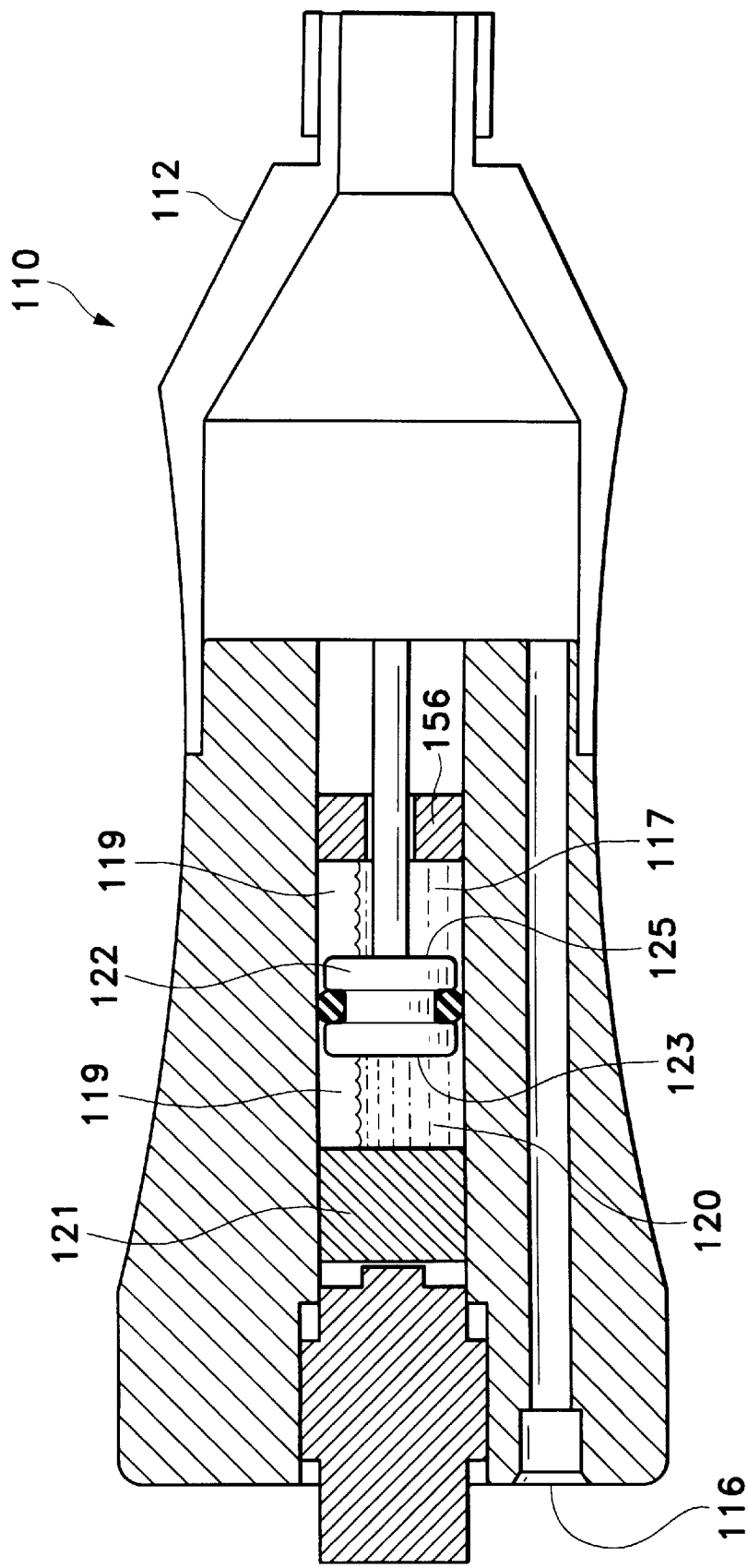
FIGS. 4A–4C ares schematic, cross-sectional view of a second embodiment of the handpiece of the present invention.
Figure 4B:
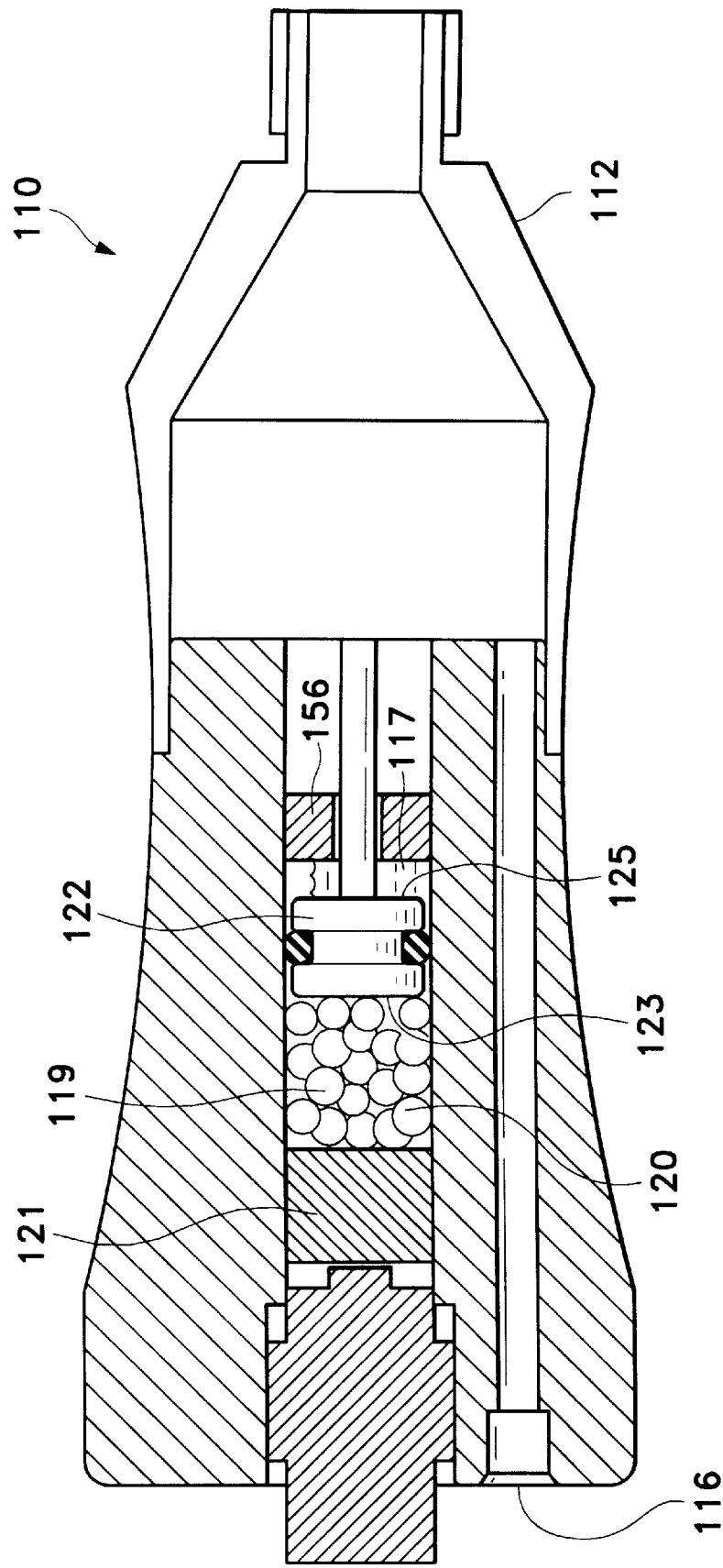
Figure 4C:
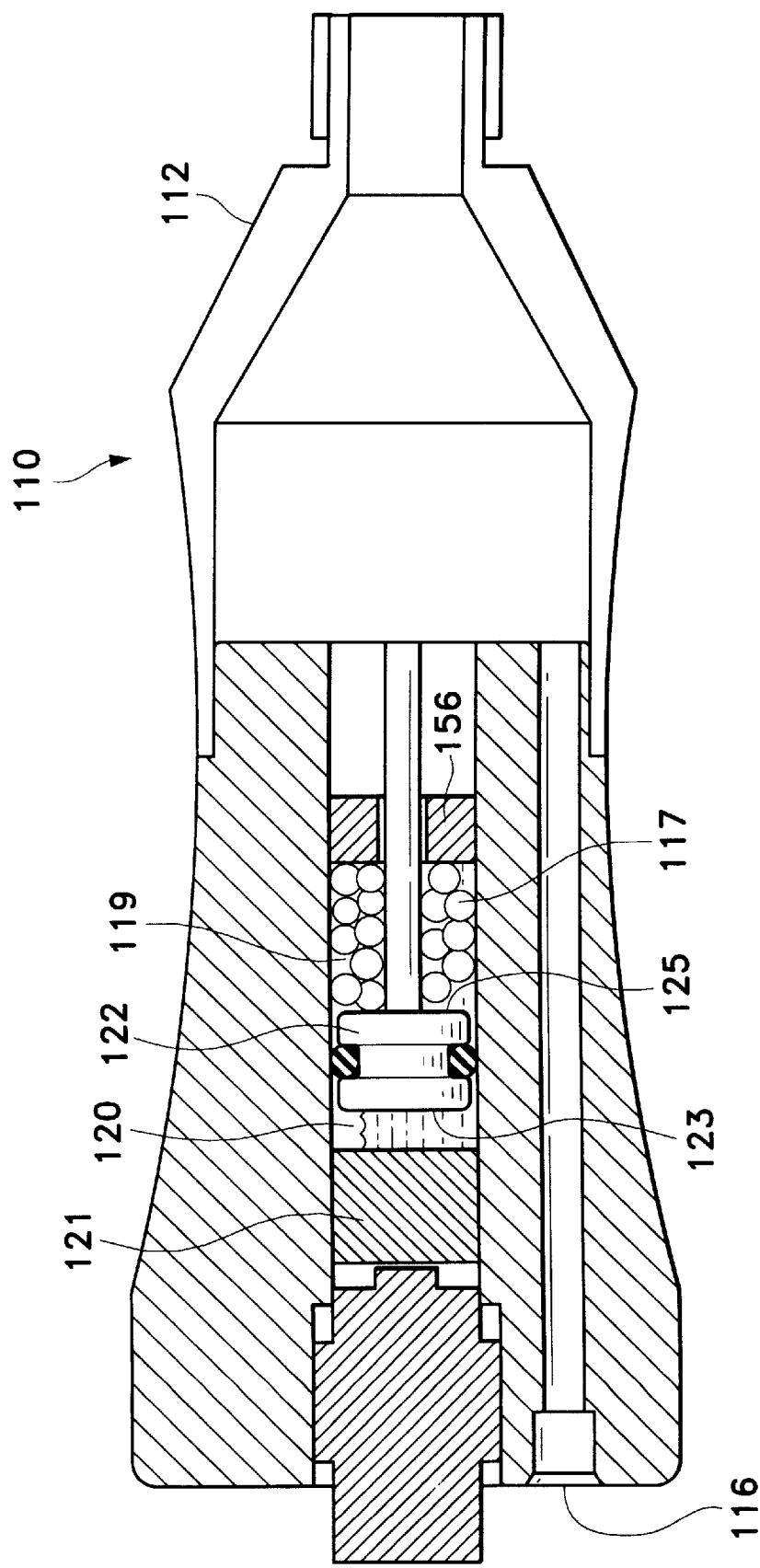

In the second embodiment of the present invention illustrated in FIGS. 4A–4C, pumping chamber 119 of handpiece 110 contains proximal pumping chamber 120 formed between proximal electrode 121 and piston 122 and distal pumping chamber 117 formed between distal electrode 156 and piston 122. Pumping chamber 120 and 117 contain both a conductive surgical fluid and a gas. In operation, electrical current is supplied to proximal electrode 121 and flows through the fluid to electrode 123 located on the proximal end of piston 122., thereby boiling the fluid. As the fluid boils, piston 122 is forced distally, as shown in FIG. 4B. Electrical current is then alternatively supplied to distal electrode 156 and flows through the fluid to electrode 125 located on the distal end of piston 122., thereby boiling the fluid located in distal pumping chamber 117. The fluid boils in pumping chamber 117 at the same time the steam or gas in pumping chamber 120 is cooling and condensing back to a liquid, and piston 122 is forced proximally, as shown in FIG. 4C. Alternating the boiling of the fluid between pumping chambers 120 and 117 forces piston 122 to reciprocate proximally and distally without the use of spring 36. The numbers in FIGS. 4A–4C are identical to the numbers in FIGS. 1–2 except for the addition of "100" in FIGS. 4A–4C.

While only two embodiments of the handpiece of the present invention is disclosed, any handpiece producing adequate pressure pulse force, rise time and frequency may also be used. For example, any suitable handpiece producing a pressure pulse that permits between 0 and 5000 cycles per minute.

As seen in FIG. 3, one embodiment of control system 300 for use in operating handpiece 310 includes control module 347, RF amplifier 312 and function generator 314. Power is supplied to RF amplifier 312 by DC power supply 316, which preferably is an isolated DC power supply. Control module 347 may be any suitable microprocessor, and may receive input from operator input device 318. Function generator 314 provides the electric wave form to amplifier 312 and preferably operates at greater than 250 KHz to help minimize corrosion.

In use, control module 347 receives input from surgical console 320. Console 320 may be any commercially available surgical control console such as the LEGACY® SERIES TWENTY THOUSAND® surgical system available from Alcon Laboratories, Inc., Fort Worth, Tex. Console 320 is connected to handpiece 310 through irrigation line 322 and aspiration line 324, and the flow through lines 322 and 324 is controlled by the user via footswitch 326. Irrigation and aspiration flow rate information in handpiece 310 is provided to control module 347 by console 320 via interface 328, which may be connected to the ultrasound handpiece control port on console 320 or to any other output port. Control module 347 uses footswitch 326 information provided by console 320 and operator input from input device 318 to generate two control signals 330 and 332. Signal 332 is used to operate pinch valve 334, which controls the fluid flowing from fluid source 336 to handpiece 310. Fluid from fluid source 336 is heated in the manner described herein. Signal 330 is used to control function generator 314. Based on signal 330, function generator 314 provides a wave form at the operator selected frequency and amplitude determined by the position of footswitch 326 to RF amplifier 312 which is amplified to advance the powered wave form to handpiece 310 to create the desired motion.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

We claim:

1. A surgical handpiece, comprising:
   a) a body; and
   b) a pumping chamber formed internal to the body between a first electrode and a piston, the piston having a second electrode and being able to reciprocate within the pumping chamber.

2. The handpiece of claim 1 wherein the pumping chamber is capable of boiling a conductive fluid when electrical current is passed between the first electrode and the second electrode.

3. A surgical handpiece, comprising:
   a) a body having an internal irrigation lumen and an internal aspiration lumen; and
   b) a pumping chamber formed within the body and having a first electrode and a second electrode across which electrical current will flow, the second electrode being formed on a piston that reciprocates within the pumping chamber.

4. The handpiece of claim 3 wherein electrical current flowing across the electrodes is capable of boiling a fluid contained between the electrodes.

5. A surgical handpiece, comprising:
   a) a body; and
   b) a pumping chamber formed within the body between a proximal electrode and a distal electrode; and
   c) a reciprocating piston located within the pumping chamber, the piston separating the pumping chamber into a proximal pumping chamber and a distal pumping chamber.

6. The handpiece of claim 5 wherein the piston reciprocates within the pumping chamber in response to electrical current flowing through the distal electrode and the proximal electrode.

* * * * *